US009061046B2

(12) United States Patent
Broekaert et al.

(10) Patent No.: US 9,061,046 B2
(45) Date of Patent: Jun. 23, 2015

(54) ARABINOXYLO-OLIGOSACCHARIDES USEFUL AGAINST GASTROINTESTINAL INFECTIONS

(75) Inventors: Willem Broekaert, Dilbeek (BE); Jan Delcour, Heverlee (BE)

(73) Assignee: Cargill, Incorporated, Wayzata, MN (US)

( * ) Notice: Subject to any disclaimer, the term of this patent is extended or adjusted under 35 U.S.C. 154(b) by 137 days.

(21) Appl. No.: 12/680,435

(22) PCT Filed: Sep. 29, 2008

(86) PCT No.: PCT/EP2008/063044
§ 371 (c)(1),
(2), (4) Date: Mar. 26, 2010

(87) PCT Pub. No.: WO2009/040445
PCT Pub. Date: Apr. 2, 2009

(65) Prior Publication Data
US 2012/0015902 A1    Jan. 19, 2012

(30) Foreign Application Priority Data
Sep. 28, 2007  (GB) .................................. 0718974.9

(51) Int. Cl.
| | | |
|---|---|---|
| *A61K 31/716* | (2006.01) | |
| *A23L 1/10* | (2006.01) | |
| *A23L 1/30* | (2006.01) | |
| *A23L 1/308* | (2006.01) | |
| *A61K 31/00* | (2006.01) | |
| *A61K 31/715* | (2006.01) | |

(52) U.S. Cl.
CPC ............ *A61K 31/716* (2013.01); *A23L 1/1016* (2013.01); *A23L 1/30* (2013.01); *A23L 1/308* (2013.01); *A61K 31/00* (2013.01); *A61K 31/715* (2013.01)

(58) Field of Classification Search
None
See application file for complete search history.

(56) References Cited

U.S. PATENT DOCUMENTS

| 4,494,530 A | 1/1985 | Jansma et al. |
|---|---|---|
| 5,362,502 A | 11/1994 | Slade et al. |
| 5,429,828 A | 7/1995 | Fodge et al. |
| 5,614,501 A | 3/1997 | Richards |
| 5,622,738 A | 4/1997 | Takeuchi et al. |
| 6,033,712 A | 3/2000 | Greenshields et al. |
| 6,132,716 A | 10/2000 | Morgan et al. |
| 6,147,206 A | 11/2000 | Doner et al. |
| 6,162,473 A | 12/2000 | Fodge et al. |
| 6,241,983 B1 * | 6/2001 | Paul et al. ..................... 424/93.4 |
| 6,558,930 B2 | 5/2003 | Hwang et al. |
| 6,720,014 B1 | 4/2004 | Short et al. |
| 7,033,633 B2 | 4/2006 | Poulsen et al. |
| 2001/0020091 A1 | 9/2001 | Buchanan et al. |
| 2002/0037331 A1 | 3/2002 | Hwang et al. |
| 2002/0195213 A1 | 12/2002 | Izumi et al. |
| 2005/0118299 A1 * | 6/2005 | Vickers et al. ..................... 426/2 |
| 2007/0207132 A1 | 9/2007 | Speelmans et al. |
| 2008/0102162 A1 | 5/2008 | Delcour et al. |
| 2010/0035302 A1 | 2/2010 | Broekaert et al. |
| 2011/0020498 A1 | 1/2011 | Broekaert et al. |

FOREIGN PATENT DOCUMENTS

| EP | 0 856 259 A1 | 8/1998 |
|---|---|---|
| EP | 0 904 784 A1 | 3/1999 |
| EP | 1 175 905 A1 | 1/2002 |
| EP | 0 463 706 B1 | 3/2003 |
| EP | 1 137 424 B1 | 4/2004 |
| EP | 1 418 819 B1 | 11/2005 |
| FR | 2 811 997 | 1/2002 |
| JP | 02-001701 | 1/1990 |
| JP | 2303459 | 12/1990 |
| JP | 4309501 A | 11/1992 |
| JP | 5112455 A | 5/1993 |
| JP | 06-217761 | 8/1994 |
| JP | 10120704 A | 5/1998 |
| JP | 10237107 A | 9/1998 |
| JP | 2000-501935 | 2/2000 |
| JP | 2005-500807 | 1/2005 |
| WO | WO 91/04673 | 4/1991 |
| WO | WO 95/23514 | 9/1995 |
| WO | WO 96/06935 | 3/1996 |
| WO | WO 97/09423 | 3/1997 |
| WO | WO 97/20920 | 6/1997 |
| WO | WO 97/27293 A1 | 7/1997 |
| WO | WO 98/54305 | 12/1998 |
| WO | WO 99/30570 A1 | 6/1999 |
| WO | WO 01/33973 A2 | 5/2001 |
| WO | WO 01/42433 A2 | 6/2001 |
| WO | WO 01/67891 A1 | 9/2001 |
| WO | WO 01/89317 A2 | 11/2001 |
| WO | WO 02/24926 A1 | 3/2002 |
| WO | WO 02/051264 A2 | 7/2002 |
| WO | WO 02/067698 A1 | 9/2002 |
| WO | WO 2006/002495 A1 | 1/2006 |
| WO | WO 2006/027529 A2 | 3/2006 |
| WO | WO 2008/000050 A2 | 1/2008 |
| WO | WO 2008/098320 | 8/2008 |
| WO | WO 2009/117790 A2 | 10/2009 |

OTHER PUBLICATIONS

Gove et al., definition of prevent, Webster's Third New International Dictionary, 1963, p. 1798.*

(Continued)

*Primary Examiner* — Shaojia Anna Jiang
*Assistant Examiner* — Dale R Miller
(74) *Attorney, Agent, or Firm* — Clark & Elbing LLP (57) ABSTRACT

The present invention relates to the use of oligosaccharides derived from arabinoxylan for use in the prevention and treatment of gastrointestinal infection. More particularly the invention provides a method for preventing or reducing the gastrointestinal infection of a animal or human being with bacteria associated with gastroenteritis through the supplementation of their diets with the said oligosaccharides.

14 Claims, 3 Drawing Sheets

(56) References Cited

OTHER PUBLICATIONS

"Overview of Gastroenteritis", Merck Manual Online Edition, [retrieved on Apr. 3, 2012] from the Internet http://www.merckmanuals.com/home/print/. Revision Sep. 2007.*

Karmali et al., CMA Journal, 1979, 23, 1525-1532.*

Bedford, "Factors Influencing the Use of Enzymes in Cereal-Based Diets," In *Recent Advances in Enzymes in Grain Processing*, 19:1-9 (2003).

International Search Report WO 2008/000050 A3, Jan. 29, 2008 for PCT/BE2007/000072.

Carr et al., "Viability of Bifidobacteria in Yogurt Products," *Abstracts of the General Meeting of the American Society for Microbiology*, 102nd General Meeting of the American Society for Microbiology, Salt Lake City, UT, May 19-23, 2002, Session 102:Abstract O-7, May 20, 2002.

Gibson et al., "Regulatory Effects of Bifidobacteria on the Growth of Other Colonic Bacteria," *J. Appl. Bacteriol*. 77:412-420, 1994.

Grootaert et al., "Microbial Metabolism and Prebiotic Potency of Arabinoxylan Oligosaccharides in the Human Intestine," *Trends in Food Science and Technology* 18:64-71, 2007.

International Search Report for PCT/EP2008/063044, mailed May 18, 2009.

Written Opinion for PCT/EP2008/063044, mailed May 18, 2009.

International Preliminary Report on Patentability for PCT/EP2008/063044, mailed Apr. 8, 2010.

Communication pursuant to Article 94(3) EPC for European Patent Application No. 08804894.7, dated Aug. 23, 2013 (5 pages).

Gibson, "Functional foods: probiotics and prebiotics," Culture 28:1-3 (2007).

Gibson et al., "Prebiotics and resistance to gastrointestinal infections," Br J Nutr. 93 Suppl. 1:S31-S34 (2005).

Niewold et al., "Dietary inclusion of arabinoxylan oligosaccarides (AXOS) down regulates mucosal responses to a bacterial challenge in a piglet model," Journal of Functional Foods 4:626-635 (2012).

Abe et al., "Effect of Administration of Bifidobacteria and Lactic Acid Bacteria to Newborn Calves and Piglets," *J. Dairy Sci.* 78:2838-2846 (1995).

Advisory Action for U.S. Appl. No. 10/487,184, dated Nov. 15, 2007.

Advisory Action for U.S. Appl. No. 10/487,184, dated Apr. 20, 2010.

Annison et al., "Analysis of Wheat Arabinoxylans from a Large-Scale Isolation," *Carbohydrate Polymers* 19: 151-159 (1992).

Aust et al., "Estimation of Available Energy of Dietary Fibres by Indirect Calorimetry in Rats," *Eur. J. Nutr.* 40:23-29 (2001).

Bach Knudsen and Hansen, "Gastrointestinal Implications in Pigs of Wheat and Oat Fractions, 1. Digestibility and Bulking Properties of Polysaccharides and other Major Constituents" *Br. J. Nutr.* 65(2):217-232 (1991).

Bedford, "Factors Influencing the Use of Enzymes in Cereal-Based Diets," In *Recent Advances in Enzymes in Grain Processing*, 19:1-9 (2002).

Bedford and Classen, "Reduction of Intestinal Viscosity through Manipulation of Dietary Rye and Pentosanase Concentration Is Effected Through Changes in the Carbohydrate Composition of the Intestinal Aqueous Phase and Results in Improved Growth Rate and Food Conversion Efficiency of Broiler Chicks," *J. Nutr.* 122:560-569 (1992).

Bird, "Performance Improvements Following Enzyme Supplementation of Wheat- and Barley-Based Poultry Diets," in *Enzymes in Poultry Swine Nutr.* Proceedings of the First Chinese Symposium on Feed Enzymes, Nanjing Agricultural University, Nanjing, P.R. China, May 6-8, 1996. pp. 73-87. Published Jun. 1997.

Bonneau and Laarveld, "Biotechnology in Animal Nutrition, Physiology and Health," *Livest. Prod. Sci.* 59.223-241 (1999).

Boros and Marquardt, "Improvement of Nutritional Value of Rye by Enzyme Application", *Hodowla Roslin Aklimatyzacja I Nasiennictwo*, 38:95-110 (1994).

Brennan and Singh, *Economic Assessment of Improving Nutritional Characteristics of Feed Grains*, Report prepared for Grains Research and Development Corporation, Economic Research Report No. 3, Wagga Wagga (2000).

Brief filed on behalf of DF3 SAS and Cosucra Groupe Warcoing in opposition of EP 1 758 470, dated Feb. 17, 2011, including Annex 1 and Annex 2.

Burton-Freeman, "Dietary Fiber and Energy Regulation," *J. Nutr.* 130(2S Suppl.): 272S-275S (2000).

Caprita et al., "Biochemical Aspects of Non-Starch Polysaccharides," *Scientific Papers: Animal Science and Biotechnologies* 43:368-375 (2010).

Carvalheiro et al., "Optimization of Brewery's Spent Grain Dilute-Acid Hydrolysis for the Production of Pentose-Rich Culture Media," *Appl. Biochem. Biotechnol.* 113-116:1059-1072 (2004). (Abstract only).

"Cereal Grains and Their By-Products," www.asasea.com abstract, printed Mar. 20, 2003.

Choct, "Feed Non-Starch Polysaccharides: Chemical Structures and Significance", *ASA Southeast Asia*, p. 1-9.; www.asasea.wm/an08.97.html, date omitted on IDS but reference of record has date of Feb. 18, 2004.

Choct and Annison, "Anti-Nutritive Effect of Wheat Pentosans in Broiler Chickens: Roles of Viscosity and Gut Microflora," *Br. Poult. Sci.* 33:821-834 (1992).

Choct and Kocher, "Non-Starch Carbohydrates: Digestion and its Secondary Effects in Monogastrics," *Proc. Nutr. Soc. Aust.* 24:31-38 (2000).

Cloetens, "In Vivo Evaluation of the Gastrointestinal Effects of Arabinoxylan-Oligosaccharides in Healthy Subjects," *Doctoral Thesis in Medical Sciences, Katholieke Universiteit Leuven* (Apr. 2009).

Close, "Producing Pigs Without Antibiotic Growth Promoters," *Advances in Pork Production* 11:47-56 (2000).

Communication from Examiner for GB Application No. 0612976.1, dated Nov. 1, 2006.

Cosucra, "Quantités d'oligosaccharides prébiotiques vendus par la société," dated Jul. 3, 2009; cited in opposition of European Patent Application No. EP 02766984.5 on Aug. 17, 2009.

Courtin et al., "Determination of Reducing End Sugar Residues in Oligo- and Polysaccharides by Gas-Liquid Chromatography", *Journal of Chromatography A*, 866:97-104 (2000).

Courtin et al., "Dietary Inclusion of Wheat Bran Arabinoxylooligosaccharides Induces Beneficial Nutritional Effects of Chickens," *Cereal Chem*. 85(5):607-613 (2008).

Courtin and Delcour, "Physicochemical and Bread-Making Properties of Low Molecular Weight Wheat-Derived Arabinoxylans," *J. Agric. Food Chem.* 46:4066-4073 (1998).

Crittenden et al., "In Vitro Fermentation of Cereal Dietary Fibre Carbohydrates by Probiotic and Intestinal Bacteria," *J. Sci. Food Agric.* 82:781-789 (2002).

Data Sheet of Cellulase <Onozuka> RS from *Trichoderma viride*, Copyright 2007/SERVA GmbH.

Data Sheet of Pentopan® Mono BG, Novozymes A/S Denmark (2008).

De Preter et al., "The In Vivo Use of the Stable Isotope-Labelled Biomarkers Lactose-[$^{15}$N]ureide and [$^2$H$_4$]Tyrosine to Assess the Effects of Pro- and Prebiotics on the Intestinal Flora of Healthy Human Volunteers," *British Journal of Nutrition* 92:439-446 (2004).

Egi et al., "Arabinoxylans and Their Behavior During Malting and Brewing," *MBAA TQ* 41(3):248-267 (2004).

E-mail Communication between Joël Bazin of Novozymes France S.A. and Joseph Fockedey of Cosucra Groupe Warcoing and its English translation, dated Sep. 1, 2010 and Sep. 6, 2010.

English Language Translation of the Office Action issued in connection with Chinese Patent Application No. 200580022193, dated Feb. 12, 2010.

Fastinger, "Development of a Novel Value-Added Distillers Dried Grains with Solubles: Effects on Amino Acid and Energy Digestibility in Pigs," Dissertation, Ohio State University (2005).

Faulds et al., "Specificity of Feruloyl Esterases for Water-Extractable and Water-Unextractable Feruloylated Polysaccharides: Influence of Xylanase," *Journal of Cereal Science* 38:281-288 (2003).

Glitsøet al., "Degradation of Rye Arabinoxylans in the Large Intestines of Pigs," *J. Sci. Food Agric.* 79:961-969 (1999).

Grootaert et al., "Microbial Metabolism and Prebiotic Potency of Arabinoxylan Oligosaccharides in the Human Intestine," *Trends in Food Science & Technology* 18:64-71 (2007).

(56) References Cited

OTHER PUBLICATIONS

Groot Wassink et al., "Fractionation of Crude Pentosanase (Arabinoxylanase) for Improvement of the Nutritional Value of Rye Diets for Broiler Chickens," *J. Sci. Food Agric.* 46(3): 289-300 (1989).

Hoffmann et al., "$^1$H-N.M.R. Study of Enzymically Generated Wheat-Endosperm Arabinoxylan Oligosaccharides: Structures of Hepta-to Tetradeca-Saccharides Containing Two or Three branched Xylose Residues," *Carbohydr. Res.* 223: 19-44 (1992).

Hoffmann et al., "Structural Characteristics of the Warm-Water-Soluble Arabinoxylans from the Tailings of the Soft Wheat Variety Kadet," *Carbohydrate Polymers* 16:275-289 (1991).

Instruction Manual for Cellulase "Onozuka" R-10 from *Trichoderma viride* cited in brief filed on behalf of DF3 SAS and Cosucra Groupe Warcoing in opposition of EP 1 758 470, dated Feb. 17, 2011.

International Preliminary Report on Patentability for PCT/BE2007/000072, issued Jan. 6, 2009, mailed Jan. 15, 2009. Includes written opinion, mailed Jan. 29, 2008.

Interview Summary for U.S. Appl. No. 10/487,184, dated Dec. 10, 2008.

Kitta (Shigeki Kitta, Executive General Manager, Consumer Health Products Division, Suntory Limited Dojimahama 2-1-40, Kita-ku, Osaka, Osaka 530-8203, Japan). "Beginning of Sales," [Letter]. Letter to: Joseph Fockedey (Cosucra, Rue de la Sucrerie, 1, 7740 Warcoing, Belgium). Sep. 5, 2007.

Kontula et al., "Oat Bran β-gluco- and Xylo-Oligosaccharides as Fermentative Substrates for Lactic Acid Bacteria," *Int. J. Food Microbiol.* 45: 163-169 (1998).

Kurmann and Rasic, Chapter 6, "The Health Potential of Products Containing Bifidobacteria," in *Therapeutic Properties of Fermented Milks*, Robinson ed., pp. 117-157 (1991).

Livesey, "The Energy Values of Dietary Fibre and Sugar Alcohols for Man," *Nutr. Res. Rev.* 5(1):61-84 (1992).

Maes et al., "Relative Activity of Two Endoxylanases Towards Water-Unextractable Arabinoxylans in Wheat Bran," *Journal of Cereal Science* 39:181-186 (2004).

Maes, "Structural Features of Wheat (*Triticum aestivum*) Bran Arabinoxylan Fractions Extracted with Endoxylanases or Alkaline Media," *Doctoral Dissertation in Agriculture, Katholieke Universiteit Leuven*, Belgium (Aug. 2004).

Majerowicz, (Bredema, 38 Avenue de l'Opéra 75002 Paris, France, mm@bredema.com); Joseph Fockedey (Cosucra, Rue de la Sucrerie, 1, 7740 Warcoing, Belgium, Jfockedey@cosucra.com ). "Opposition au Brevet EP 1 418 819 Bl," [electronic mail on the internet]. Message to: Stephanie Patarin (Bredema, 38 Avenue de l'Opéra 75002 Paris, France; stp@bredema.com) and Eric Enderlin (Bredema, 38 Avenue de l'Opéra 75002 Paris, France; een@bredema.com), Marc Majerowicz, (Bredema, 38 Avenue de l'Opéra 75002 Paris, France; mm@bredema.com), Yann Dugenet (yann.dugenet@wanadoo. com), Mingan Choct (Professor (seconded to Poultry CRC), Faculty of Arts and Sciences, School of Environmental and Rural Sciences, University of New England, Armidale NSW 2351 Australia, mchoct@une.edu.au), Joseph Fockedey (Cosucra, Rue de la Sucrerie, 1, 7740 Warcoing, Belgium; Jfockedey@cosucra.com ). Sep. 10, 2007, 9:45 AM. French and English languages. The product is a food additive containing about 70 of arabinoxylans, having a molecular mass between 5000 and 758000, and is obtained in the starch industry by wet milling.

Modler, "Bifidogenic Factors—Sources, Metabolism and Applications," *Int. Dairy J.* pp. 383-389 and 391-407 (1994).

Moers et al., "Endoxylanase Substrate Selectivity Determines Degradation of Wheat Water-Extractable and Water-Unextractable Arabinoxylan," Carbohydrate Research 340:1319-1327 (2005).

Mroz et al., "Effects of Dietary Carbohydrates and Buffering Capacity on Nutrient Digestibility and Manure Characteristics in Finishing Pigs," *J. Anim. Sci.* 78(12):3096-3106 (2000).

Mul and Perry, "The Role of Fructo-Oligosaccharides in Animal Nutrition," In *Recent Advances in Animal Nutrition, Proceedings of the 28$^{th}$ University of Nottingham Feed Conference*, Cole ed., Nottingham University Press, pp. 57-79 (1994).

Notice of Allowance and Notice of Allowability for U.S. Appl. No. 12/306,943, dated Jul. 14, 2011.

Office Action for Australian Patent Application No. 2005259856, dated Mar. 11, 2010.

Office Action for Canadian Application No. 2,456,304, dated Dec. 18, 2009.

Office Action for Indian Application No. 417/DELNP/2004, dated Feb. 4, 2010.

Office Action for European Patent Application No. EP 07 784 889.3, dated Jun. 24, 2009.

Official Communication from European Patent Office for European Patent Application 07 784 889.3, dated Dec. 9, 2010.

Official Communication from European Patent Office for European Patent Application 08 804 894.7-2123, dated Feb. 9, 2011.

Office Action for U.S. Appl. No. 10/487,184, dated Jan. 4, 2007.
Office Action for U.S. Appl. No. 10/487,184, dated Jun. 14, 2007.
Office Action for U.S. Appl. No. 10/487,184, dated Sep. 17, 2008.
Office Action for U.S. Appl. No. 10/487,184, dated Jun. 17, 2009.
Office Action for U.S. Appl. No. 10/487,184, dated Jan. 5, 2010.
Office Action for U.S. Appl. No. 10/487,184, dated Mar. 10, 2011.
Office Action for U.S. Appl. No. 10/487,184, dated Aug. 18, 2011.
Office Action for Chinese Patent Application No. 200980116562.X, dated Oct. 20, 2011 (with Translation).

Pawlik et al., "Improvement of the Nutritional Value of Rye by the Partial Hydrolysis of the Viscous Water-Soluble Pentosans Following Water-Soaking or Fungal Enzyme Treatment," *Br. Poult. Sci.* 31(3):525-538 (1990).

Prosky and Hoebregs, "Methods to Determine Food Inulin and Oligofructose," *J. Nutr.* 129(Suppl):1418S-1423S (1999).

Reply to the Official Communication Under A96(2) for EP 02766984.5, submitted Jan. 10, 2005.

Rijnen et al., "Effects of Dietary Fermentable Carbohydrates on Energy Metabolism in Group-Housed Sows," *J. Anim. Sci.* 79(1):148-154 (2001).

Roberts et al., "The Influence of Dietary Composition on Energy Intake and Body Weight," *J. Am. Coll. Nutr.* 21(2): 140S-145S (2002).

Rokey, G.J., "Petfood and Fishfood Extrusion," The Technology of Extrusion Cooking 144-145 (1995).

Ross Tech 99/37, "Role of Antibiotic as Growth Promoter," printout from world.rossbreeders.com (1999); cited in opposition of European Patent Application No. EP 02766984.5 on Aug. 17, 2009.

Schooneveld-Bergmans, "Physicochemical Characteristics of Wheat Bran Glucuronoarabinoxylans," *J. Cereal Sci.* 29(1):49-61 (1999).

Search Report for GB Application No. 0612976.1, mailed Oct. 30, 2006, date of search Oct. 27, 2006.

Shiiba et al., "Purification and Characterization of Two Arabinoxylans from Wheat Bran," *Cereal Chem.* 70(2):209-214 (1993).

Smith et al., "Energy Balance and Thermogenesis in Rats Consuming Nonstarch Polysaccharides of Various Fermentabilities," *Am. J. Clin. Nutr.* 68(4):802-819 (1998).

Sørensen et al., "Efficiencies of Designed Enzyme Combinations in Releasing Arabinose and Xylose from Wheat Arabinoxylan in an Industrial Ethanol Fermentation Residue," *Enzyme and Microbial Technology* 36:773-784 (2005).

Sørensen et al., "Optimization of Reaction Conditions for Enzymatic Viscosity Reduction and Hydrolysis of Wheat Arabinoxylan in an Industrial Ethanol Fermentation Residue," *Biotechnol. Prog.* 22:505-513 (2006).

Supplemental Search Report for British Application No. GB0612976.1, dated Nov. 1, 2006.

Swennen et al., "Ultrafiltration and Ethanol Precipitation for Isolation of Arabinoxylooligosaccharides with Different Structures," *Carbohydrate Polymers* 62:283-292 (2005).

Van Craeyveld et al., "Structurally Different Wheat-Derived Arabinoxylooligosaccharides Have Different Prebiotic and Fermentation Properties in Rats," *Journal of Nutrition* 138:2348-2355 (2008).

Van Laere et al., "Fermentation of Plant Cell Wall Derived Polyaccharides and Their Corresponding Oligosaccharides by Intestinal Bacteria," *J. Agric. Food Chem.* 48(5):1644-1652 (2000).

(56) References Cited

OTHER PUBLICATIONS

Van Loo et al., "Functional Food Properties of Non-Digestible Oligosaccharides: A Consensus Report from the ENDO Project (DGXII AIRII-CT94-1095)," *Br. J. Nutr.* 81(2):121-132 (1999).

Voragen, "The Cell Wall and its Components in Cereals and Pulse Grains, Consequences on Nutritional Value," *Cah. Options Mediterr.* 26:119-123 (1997).

Yamada et al., "Preparation of a New Arabinoxylooligosaccharide from Wheat Bran Hemicellulose and Its Structure," *Biosci. Biotech. Biochem.* 58(2):288-292 (1994).

Cloetens et al., "The Bifidogenic Potential of Arabinoxylo-Oligosaccharides in Healthy Volunteers Depends on the Degree of Polymerisation," Abstract W1382, *Gastro.* 134(4):A-692 (2008).

Cloetens et al., "The Effect of Two Different Doses of Arabinoxylo-Oligosaccharides and Oligofructose Enriched Inulin on the Colonic Ammonia Metabolism in Healthy Volunteers," Abstract 1383, *Gastro.* 134(4): A-693 (2008).

International Preliminary Report on Patentability for International Application No. PCT/BE2009/000020 dated Mar. 18, 2010 (date of completion and mailing of report).

International Search Report WO 2008/000050 A3, Jan. 29, 2008.

International Search Report for PCT International Application No. PCT/BE2009/000020 dated Sep. 23, 2009 (date of completion of search) and Oct. 13, 2009 (date of mailing of report).

Swennen et al., "Large-Scale Production and Characterisation of Wheat Bran Arabinoxylooligosaccharides," *J. Science and Food Agric.* 86(11):1722-1731 (2006).

Written Opinion of the International Searching Authority of PCT International Application No. PCT/BE2009/000020 dated Sep. 23, 2009 (date of completion of this opinion) and Oct. 13, 2009 (date of mailing of this opinion).

Yamada et al., "Structure and Properties of Oligosaccharides from Wheat Bran," *Cereal Foods World* 38(4):490-492 (1993).

Reply to Written Opinion for International Patent Application No. PCT/BE2009/000020 dated Jan. 29, 2010.

*Association des Amidonneries de Céréales de l'Union Européenne*, printout from http://www.authorstream.com/Presentation/miloung-16703-7-Labelling-wheat-starch-derivatives-AAC-members-Why-new-EU-rules-specific-forwheat-seedcount-presentation-002-News-Reports-ppt-powerpoint/, "Changes in the EU Labeling Legislation," (Nov. 19, 2003).

Beaugrand et al., "Impact and Efficiency of GH10 and GH11 Thermostable Endoxylanases on Wheat Bran and Alkali-Extactable Arabinoxylans," *Carbohydrate Research* 339:2529-2540 (2004).

Clayton, "The Extraction and Ion-Exchange Chromatography of Buffer-Soluble and Gluten Proteins of Wheat Flour," *Cereal Chemistry* 43:495-516 (1966).

Fang et al., "Influence of Temperature on the Retention Behaviour of Proteins in Cation-Exchange Chromatography," *Journal of Chromatography A* 729(1-2):49-66 (1996), Abstract only.

Katapodis amd Christakopoulos, "Enzymic Production of Feruloyl Xylo-Oligosaccharides from Corn Cobs by a Family 10 Xylanase from *Thermoascus aurantiacus*," *LWT* 41:1239-1243 (2008), e-published Sep. 1, 2007.

Official Communication from the European Patent Office for European Patent Application No. 09725460.1, dated Feb. 15, 2011.

Official Communication from the European Patent Office for European Patent Application No. 09725460.1, dated Feb. 21, 2011.

Official Communication from the European Patent Office for European Patent Application No. 09725460.1, dated Feb. 28, 2011.

Purolite Company, "Corn Sweetener Refining with Ion Exchange Resins," (2007).

Roberfroid and Slavin, "Nondigestible Oligosaccharides," *Critical Reviews in Food Science and Nutrition* 40(6):461-480 (2000).

Swennen, "Production, Characterisation, and Functionality of Arabinoxyooligosaccharides with Different Structures," *Dissertationes de Agricultura, Katholieke Universiteit Leuven* (Feb. 2007).

Yuan et al., "Antioxidant Activity of Feruloylated Oligosaccharides from Wheat Bran," *Food Chemistry* 90:759-764 (2005).

* cited by examiner

ARABINOXYLO-OLIGOSACCHARIDES USEFUL AGAINST GASTROINTESTINAL INFECTIONS

CROSS REFERENCE TO RELATED APPLICATIONS

This application is the U.S. national stage of International Application No. PCT/EP2008/063044, filed Sep. 29, 2008, which claims the benefit of UK Patent Application No. GB0718974.9, filed Sep. 28, 2007.

FIELD OF THE INVENTION

The present invention relates to the use of oligosaccharides derived from specific arabinoxylans in the treatment and/or prevention of gastrointestinal infections in animals and human beings. More particularly the invention relates to a method for preventing or reducing the gastrointestinal infection of an animal or a human being with bacteria associated with gastroenteritis by supplementing their diets with the said oligosaccharides.

BACKGROUND OF THE INVENTION

Gastroenteritis is a significant problem in animal husbandry as well as in human medicine. Gastroenteritis is primarily caused by food-borne pathogens, such as bacterial species belonging to the *Salmonella, Campylobacter, Escherichia, Listeria, Clostridium*, or *Shigella* geni, which typically ingress through the lower parts of the gastrointestinal tract. In animal husbandry, gastrointestinal infections can be relatively well controlled by inclusion of sub-therapeutic doses of antibiotics in the feed. However, the preventative use of antibiotics is either banned or strongly discouraged in many countries due to the growing emergence of antibiotic-resistant pathogens. Likewise, antibiotics in human medicine are nowadays subject to more strict use policies. Alternative treatments include the use of dietary supplements such as short or medium chain organic acids, manno-oligosaccharides which interfere with mucosal attachment of pathogens, or fructan-based oligosaccharides which stimulate beneficial gut microbiota. Inoculation of animals with competitive-exclusion microbiota is another form of treatment.

There is a need to extend the range of preventive and therapeutic treatment methods against gastrointestinal infections, especially since some of the proposed control agents do not yield consistent results. For instance inulin and oligofructose have been reported to decrease the incidence of systemic infection by *Salmonella enterica* serovar Typhimurium and *Listeria monocytogenes* in mice, whereas in rats it increased the levels of *S. enterica* ser. Enteritidis in the gut and promoted systemic translocation. Likewise, inclusion of a oligofructose from Jerusalem artichokes in chicken diet promoted colonisation of chicken caeca by *Salmonella enterica* ser. Typhimurium, whereas oligofructose from chicory roots had the opposite effect.

Arabinoxylans are polysaccharides that occur in the cell wall of most monocotyledonous plant species, and are therefore abundantly present in cereal-based diets. They comprise a main chain of $\beta$-1,4-linked D-xylopyranosyl units to which O-2 and/or O-3 □-L-arabino-furanosyl units are linked, together with minor substituents such a alpha-(methyl)glucuronyl, acetyl, feruoyl, and/or p-coumaryl groups. Arabino-oligosaccharides (hereinafter referred as AXOS), i.e. oligosaccharides derived by partial hydrolysis of arabinoxylan, have been demonstrated to stimulate the growth and improve the feed intake when added to the diet of animals (WO03/015533), whereas uncleaved arabinoxylan is well known to hamper efficient food utilisation. AXOS has also been shown to stimulate beneficial microflora in the caeco-colonic compartment of the gastrointestinal tract (WO06/002495), while arabinoxylan promotes fermentation in the ileum. The effect of dietary supplement with arabinoxylan on the attachment *S. enterica* ser. Enteritidis to the ileum of broiler chicks has been investigated. It was found that dietary addition of 0.5% arabinoxylan from corn hull (average molecular weight 500,000) slightly promoted *Salmonella* attachment when the chicks were raised at 23° C., whereas a slight decrease in attachment was observed in chicks raised at the suboptimal temperature of 29° C., although none of the effects were significant.

SUMMARY OF THE INVENTION

In a first object the present invention provides a method for preventing or reducing the infection of an animal or a human being with bacteria associated with the occurrence of gastroenteritis, comprising enterally administering arabinoxylo-oligosaccharides having an average degree of polymerization between 3 and 50 and an average degree of substitution between 0.15 and 0.35. The present invention further provides the use of such arabinoxylo-oligosaccharides in the production of a human or veterinary medicine for preventing or reducing the infection of a subject with bacteria associated with the occurrence of gastroenteritis.

DETAILED DESCRIPTION OF THE INVENTION

The pathogenic sequence of a bacterial gastrointestinal infection starts with the survival and growth of a pathogen in the lumen of the gastrointestinal tract. Therefore, the strengthening of a subject's colonization resistance against pathogens is an important strategy in the prevention of gastrointestinal infections. Moreover, an improved colonization resistance not only decreases the occurrence of infections but also reduces the severity of an incurred infection. The present invention shows that the oral administration of an appropriate amount of certain arabinxylo-oligosaccharides significantly improves the gastrointestinal colonization resistance of a subject against pathogenic bacteria. Indeed, supplementing such arabinxylo-oligosaccharides to the feed of a model animal orally infected with a gastrointestinal pathogen resulted in a clearly lower fecal excretion of that model pathogen in the faeces in the period following the infection. Moreover, the oral administration of such arabinoxylo-oligosaccharides reduced the translocation of the pathogen towards internal organs. Therefore, in a first object the present invention provides a method to reduce or prevent the infection of a human being or an animal with gastro-intestinal pathogenic bacteria. Said method comprises enterally administering a therapeutically effective amount of specific arbinoxylo-oligosaccharides to said human being or animal prior to or during the occurrence of an infection. Amongst others, the method of the present invention can be used to reduce or prevent the infection by gastro-intestinal pathogenic bacteria belonging to the *Salmonella, Campylobacter, Escherichia, Listeria, Clostridium, cholera, Vibrio, Yersinia, Aeromonas, Pleisomonas* or *Shigella* geni.

As used herein "arabinoxylo-oligosaccharides" refers to oligosaccharides derived from arabinoxylans comprising a main chain of β-1,4-linked D-xylopyranosyl units to which O-2 and/or O-3 α-L-arabino-furanosyl units are preferably linked. For the purpose of the present invention it is preferred that the average degree of substitution of the arabinoxylo-oligosaccharides varies between 0.15 and 0.35. Preferably, the average degree of polymerisation of the arabinoxylo-oligosaccharides used in the present invention is at least 3, more preferably at least 4, for instance at least 5. Preferably, the average degree of polymerisation of the arabinoxylo-oligosaccharides used in the present invention is at most 50, more preferably at most 20, most preferably at most 10. The average degree of substitution and the average degree of polymerisation can be determined by any method known in the art, e.g. as previously described by K. Swennen et al. in *J. Sci. Food Agric.* (2006) 86:722-731. In short, the carbohydrates in an arabinoxylo-oligosaccharides-containing preparation were hydrolysed using trifluoric acid and the resulting monosaccharides were reduced and converted to alditol acetates, which were then analyzed using gas chromatography. The total arabinoxylan-content was calculated as being 0.88 times the sum of the monosaccharides xylose and arabinose, while the average degree of substitution was determined as the arabinose-to-xylose ratio. The average degree of polymerization was calculated as the sum of the total xylose and arabinose divided by the amount of reducing end xylose.

Arabinoxylo-oligosaccharides suitable for use in the method according to the present invention can be obtained by partial hydrolysis of arabinoxylans extracted from cereals or cereal derived material. More preferably, these arabinoxylo-oligosaccharides may be obtained by hydrolysis of arabinoxylans extracted from bran, for instance wheat or rye bran.

When using the method according to the present invention for the prevention or treatment of the infection of an animal, e.g. a mammal, with gastro-intestinal pathogenic bacteria it is preferred to administer a therapeutically effective amount of the specific arabinoxylo-oligosaccharides through (together with) the feed. Preferably the animal feed is supplemented with at least 1 g, for instance at least 2 g, of arabinoxylo-oligosaccharides per kg feed. Preferably the animal feed is supplemented with at most 50 g, more preferably at most 10 g, most preferably at most 5 g, for instance at most 4 g of arabinoxylo-oligosaccharides per kg feed. The method of the present invention is useful as an element in the prophylaxis of livestock animals, poultry and pets. It more particularly contributes to the prophylactic management of the breeding of calves, chickens, turkeys, pigs and horses amongst others.

When using the method of the present invention in pet animals, such as cats and dogs, it may be advantageous to incorporate the daily effective amount of arabinoxylo-oligosaccharides in a daily serving of a pet food. Preferably, such pet food comprises at least 0.25 g, more preferably at least 0.5 g of arabinoxylo-oligosaccharides per daily serving of said pet food. Preferably, such pet food comprises at most 10 g, more preferably at most 5 g, most preferably at most 2.5 g of arabinoxylo-oligosaccharides per daily serving of said pet food. In a particular embodiment, it is preferred to include between 0.25 and 2 g, more preferably between 0.25 and 1 g of arabinoxylo-oligosaccharides per daily serving of a domestic cat food. In another particular embodiment, between 0.25 and 3 g, more preferably between 0.5 and 2 g of arabinoxylo-oligosaccharides are included per daily serving of food for dogs with a body weight below 10 kg, while between 0.25 and 5 g, more preferably between 0.5 and 3 g of arabinoxylo-oligosaccharides are included per daily serving of food for dogs with a body weight above 10 kg.

When using the method of the present invention in pet animals, such as cats and dogs, the daily effective amount of arabinoxylo-oligosaccharides can alternatively be included in a treat food for pets, such as biscuits or cookies. Typically, such pet treat food comprises between 0.25 and 5 g, more preferably between 0.25 and 2.5 g, for instance between 0.25 and 1 g of arabinoxylo-oligosaccharides per serving of said treat food.

When using the method according to the present invention for the prevention or treatment of the infection of a human with gastro-intestinal pathogenic bacteria, the arabinoxylo-oligosaccharides can be administered in admixture with a drink (e.g. water, milk, soft drink or beer), or in the form of a tablet, dietary supplement, candy, chewing gum or a food product. For the treatment of infants the arabinoxylo-oligosaccharides can be incorporated into an infant formula. The present invention can also be accomplished by incorporating the specific arabinoxylo-oligosaccharides in yoghurts, dairy products, fruit juice and cereal based products, such as bread, breakfast cereals, cookies and crackers amongst others. One aspect of the present invention relates to the finding that the consumption of between 0.25 and 10 g, preferably between 1 and 5 g, for instance between 1 and 3 g of arabinoxylooligosaccharides per day per human significantly reduces the presence in feces of several bacteria species associated with gastroenteritis. The reduced presence in the feces reflects a decrease of the presence of these bacteria in the intestinal flora, reducing the occurrence and severity of gastro-intestinal infections.

In a second object, the present invention relates to the use of said arabinoxylo-oligosaccharides in the production of a veterinary medicine for preventing or reducing the infection of an animal, e.g. a mammal, by gastro-intestinal pathogenic bacteria. Preferably said veterinary medicine can be incorporated into the feed of an animal in need thereof at a dose corresponding to between 1 and 50 g, more preferably between 1 and 10 g, most preferably between 1 and 5 g, for instance between 2 and 4 g of said arabinoxylo-oligosaccharides per kg feed. Preferably such veterinary medicine comprises at least 8% (w/w), more preferably at least 20% (w/w), most preferably at least 40% (w/w), for instance more than 60% by weight or more than 80% (w/w) of said arabinoxylo-oligosaccharides. Alternatively, said veterinary medicine may be added to the drinking water of the animal, preferably the veterinary medicine is added to water in order to obtain a weight concentration of said arabinoxylo-oligosaccharides between 0.25 and 20% (w/w), more preferably between 0.25 and 10% (w/w), most preferably between 0.25 and 5%. Furthermore, the said veterinary medicine may also be included into pet foods or in treat food for pets in order to supplement such pet foods with said arabinoxylo-oligosaccharides as indicated above.

In a third object the present invention relates to the use of said arabinoxylo-oligosaccharides in the production of a pharmaceutical composition for preventing or reducing the infection of a human being with gastro-intestinal pathogenic bacteria. The pharmaceutical composition of said medicament allows for the administration of a daily dose of between 0.25 and 10 g, preferably between 1 and 5 g, for instance between 1 and 3 g of arabinoxylo-oligosaccharides. Preferably said medicament comprises at least 8% (w/w), more preferably at least 20% (w/w), most preferably at least 40% (w/w), for instance more than 60% by weight or more than 80% (w/w) of said arabinoxylo-oligosaccharides.

Pharmaceutical compositions for the oral administration of the said arabinxylo-oligosaccharides can take the form of solid formulations such as, for example, tablets or capsules prepared by conventional means with one or more pharmaceutically acceptable excipients such as, but not limited to, binding agents (e.g., pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycolate); or wetting agents (e.g., sodium lauryl sulfate). The tablets can be coated by methods well known in the art. Liquid formulations for oral administration can take the form of, for example, solutions, syrups or suspensions, or they can be presented as a dry product, such as powders for dispersion or dissolution into water and/or other suitable liquid vehicles before use. Such liquid formulations can be prepared by conventional means with one or more pharmaceutically acceptable additives such as, but not limited to, suspending agents (e.g. sorbitol syrup, cellulose derivatives or hydrogenated edible fats); emulsifying agents (e.g. lecithin or acacia); aqueous or non-aqueous vehicles (e.g. almond oil, oily esters, ethyl alcohol or fractionated vegetable oils); and preservatives (e.g. methyl- or propyl-p-hydroxybenzoates or sorbic acid). These formulations can also contain buffer salts, flavouring agents, colouring agents and/or sweetening agents, as appropriate.

In a particular embodiment of this invention, said medicament may be formulated as a powder that can be admixed with a food or drink product, wherein said powder comprises between 5 and 80% (w/w), more preferably between 10 and 60% (w/w), for instance between 30 and 50% (w/w) of said arabinoxylo-oligosaccharides. Said powder preferably further comprises a flowing agent, such as silica and optionally a filler. In another particular embodiment said medicament may be formulated as a syrup, preferably comprising between 8 and 50% (w/w), more preferably between 10 and 50% (w/w), for instance between 20 and 40% (w/w) of said arabinoxylo-oligosaccharides. Said syrup may further comprise an aqueous or non-aqueous vehicle, a suspending agent, an emulsifying agent, a preservative, a buffer salt, a flavouring agent, a colouring agent and/or a sweetening agent.

The pharmaceutical formulation of this invention may also take the form of, for example, a chewing gum, a confectionery, a gel, and the like. Next to arabinoxylo-oligosaccharides, a chewing gum composition of the present invention may include a gum base and one or more of the other typical chewing gum composition components such as sweeteners, softeners, flavouring agents and the like. The chewing gum compositions of the present invention, may be coated or uncoated and may be in the form or slabs, sticks, pellets, balls amongst other forms. In a further aspect of the present invention, the chewing gum compositions may include an insoluble gum base generally comprising one or more elastomers, plasticizers, waxes, fats, oils, emulsifiers, fillers and/or texturizers. Other ingredients used in chewing gum compositions may further include both natural and artificial, sugar-based and sugarless sweeteners. Sugarless sweeteners include, but are not limited to, sugar alcohols such as sorbitol, mannitol, xylitol, hydrogenated starch hydrolysates, maltitol and the like. High intensity sweeteners such as sucralose, aspartame, neotame, salts of acesulfame and the like may also be present. Flavouring agents for use in chewing gum compositions are well known in the art and include citrus oils, peppermint oil, spearmint oil, oil of wintergreen, menthol and the like. Softeners may be present to modify the texture of the chewing gum composition. Other materials which may be present in the gum composition of the present invention include antioxidants (e.g. butylated hydroxyanisole, butylated hydroxytoluene, β-carotenes, tocopherols, colorants, flavorants and the like.

The term "confectionery" as used herein includes, but is not limited to, nougats, candies, panning goods, gel confections, fondants, lozenges, hard boiled candies, mints, troches, pastilles, microcapsules, and other solid forms including freeze dried forms (cakes, wafers, and tablets) and fast dissolving solid forms including compressed tablets and water soluble thin films. Lozenges may include discoid shaped solids comprising said arabinxylo-oligosaccharides in a flavoured base. The base may be a hard sugar candy, glycerinated gelatin, or a combination of sugar with sufficient mucilage to provide a stable form at room temperature. Lozenge compositions (compressed tablet type) typically include one or more fillers (compressible sugar), flavouring agents and/or lubricants. Details regarding the preparation of confectionery compositions can be found in Skuse's Complete Confectioner (13$^{th}$ Edition) (1957) the content of which is incorporated herein by reference.

It is preferred that the said daily effective dose of the arabinoxylo-oligosaccharides is between 1 to 10, more preferably 1 to 7, most preferably 1 to 5, for instance 3 or 4, tablets, capsules, chewing gums, or confectionery used as a pharmaceutical composition for the administration of said arabinoxylo-oligosaccharides.

A preparation comprising said arabinoxylo-oligosaccharides, which is in particular suitable for use in animal feed can be produced starting from the 'thin stillage' derived from the industrial ethanol production using cereals such as wheat, corn, barley or rye. When ethanol-containing fermented mash from cereals, produced by yeast-mediated fermentation after mashing and enzymatic liquefaction and saccharification of the starch, is distilled to obtain ethanol, a slurry comprising an aqueous phase and solids is obtained, which is typically referred to as 'whole stillage'. The whole stillage can be separated through physical separation, such as filtration, centrifugation or decantation, in a liquid aqueous fraction called 'thin stillage' and a solid-enriched fraction called 'wet distilled grains'. On dry matter basis, the thin stillage from cereal fermentation contains between 20% and 40% (w/w) of said arabinoxylo-oligosaccharides. This product can be dried by a sequence of water evaporation and drying steps, either with or without mixing with a carrier product suitable for nutritional us, such as cereal bran, to facilitate the drying process. The ratio of the thin stillage dry matter to the dry matter of the carrier product can vary between 1:0 and 1:4 (w/w on dry matter basis). The arabinoxylo-oligosaccharides content of the final dry product depends on the ratio of thin stillage over the drying carrier, and preferably contains between 8 and 40% (w/w), more preferably between 15 and 40% (w/w), most preferably between 20 and 40% (w/w), for instance between 25 and 35% of said arabinoxylo-oligosaccharides. Preferably, such arabinoxylo-oligosaccharides-containing preparations are added to the feed in amounts allowing to supplement the feed with between 1 and 50 g, more preferably between 1 and 10 g, most preferably between 1 and 5 g of said arabinoxylo-oligosaccharides. For instance, when a feed is supplemented with such thin stillage derived arabinoxylo-oligosaccharides-containing preparation comprising 20% of arabinoxylo-oligosaccharides said preparation is preferably added to the feed in an amount varying between 5 and 250 g, more preferably between 5 and 50 g, most preferably between 5 and 25 g per kg of feed. Therefore, in a fourth object the present invention provides a method for the production of a preparation between 8 and 40% of arabinoxylo-oligosaccharide. This method comprises the separation of the aqueous phase (thin stillage) from a mash of yeast fermented cereals after distillation of the ethanol from said mash (whole stillage) and subsequently drying said isolated thin stillage.

Example 1

Effect of Arabinoxylo-Oligosaccharides (AXOS) on Infection of Chickens by *Salmonella*

Materials and Methods
AXOS Preparations.
AXOS-9-0.25 was prepared from wheat bran by extraction with a glycosyl hydrolase family (GHF) 10 endoxylanase essentially as previously described (Swennen et al. cited supra), except that the step of protease treatment of the bran was omitted. This preparation has a content in polymeric xylose and arabinose of 61% on a dry matter basis, the average degree of polymerisation of AXOS is 9, and the arabinose to xylose ratio is 0.25. AXOS-3-0.25 was prepared by enzymatic extraction from wheat bran as previously described (Swennen et al. cited supra), except that that the xylanase treatment was performed for 10 hours at 50° C. with a GHF 11 xylanase (Grindamyl H640, commercially available from Danisco, Denmark) at 1.2 units per g destarched and deproteinised wheat bran, and for another 10 hours at 50° C. after addition of a GHF 10 xylanase (Shearzyme 500L, commercially available from Novozymes, Denmark) at 21 units per g destarched and deproteinised wheat bran. This preparation has a content in polymeric xylose and arabinose of 81% on a dry matter basis, the average degree of polymerisation of AXOS is 3, and the arabinose-to-xylose ratio is 0.25.

Feed Composition.
The chicks were fed a single wheat-corn-soybean diet throughout the experiment. Four different diets were prepared. The control ration contained no added AXOS and had the composition shown in Table 1. The 0.2% AXOS-3-0.25 diet consisted of the control ration with addition of 0.25% (w/w) AXOS-3-0.25, which corresponds to 0.2% AXOS content after correction for purity. The 0.2% AXOS-9-0.25 diet consisted of the control ration with 0.33% (w/w) of added AXOS-9-0.25, corresponding to 0.2% AXOS content after correction for purity. The 0.4% AXOS-9-0.25 diet consisted of the control ration with 0.66% (w/w) of added AXOS-9-0.25, corresponding to 0.4% AXOS content after correction for purity.

*Salmonella* Strain.
*Salmonella enterica* ser. Enteritidis strain SE147, a well-characterized streptomycin-resistant strain isolated from a poultry farm was used for challenge of the chickens. The strain was grown for 6 hours in Luria-Bertoni medium (LB). The number of colony-forming units (cfu) per milliliter was determined by plating 10-fold dilutions of the bacterial suspension on brilliant green agar (BGA, commercially available from Oxoid, Basingstoke, United Kingdom) containing streptomycin (100 µg/ml), whereafter the plates were incubated aerobically for 20 hours at 37° C. The initial bacterial suspensions were kept at 4° C. during plate counting, and they were diluted in phosphate buffered saline (PBS) to the appropriate density prior to use in the in vivo trial.

In Vivo Trial.
One-day-old chicks of mixed sex (224 in total, Ross breed) were housed in a bio-contained poultry house. The birds were randomly divided in 4 groups of 56 each, and each group was reared in a 1 m$^2$ surface pen with a steel rod floor. Optimal house temperature was provided by a central water heating unit and infrared bulbs and a continuous light regime was used throughout the experiment. All birds received feed and water (1 drinker per pen) ad libitum. They were orally vaccinated against coccidiosis (Paracox-5, commercially available from Schering-Plough Animal Health, Brussels, Belgium) at 3 days post-hatch. The birds were orally inoculated with 2.5×10$^9$ cfu *Salmonella* per animal at 14 days post-hatch. At the day of *Salmonella* inoculation, cloacal swabs were taken from all animals. At days 1, 3, 7, 11, 15, 19, and 23 after inoculation, cloacal swabs were taken from all animals remaining in the pens. At days 1, 3, 7, 11, 15, 19, and 23 post inoculation, a total of 8 birds per treatment group were euthanized by intravenous T61 injection and samples of caecum and spleen were taken for bacteriological analysis. The experiment was performed under supervision of the ethical committee of the Faculty of Veterinary Medicine, Ghent University.

Bacteriological Analysis.
Cloacal swabs were directly inoculated on BGA plates containing 100 µg/ml streptomycin, which were incubated overnight at 37° C. Swab cultures were scored 0 for no colonies, 1 for 1 to 10 colonies, 2 for 11 to 100 colonies, 3 for 101 to 1000 colonies, or 4 for more than 1001 colonies of *S. enterica*. After plating, the swabs were enriched by immersing in buffered peptone water and incubating overnight at 37°

C. For those samples that scored negative by direct plating of the swabs, the overnight buffered peptone water cultures were further enriched by addition of 1 mL of this suspension to 9 mL brilliant green tetrathionate broth. After overnight incubation at 37° C., a drop of this suspension was plated on BGA containing 100 µg/ml streptomycin. Samples of caeca and spleen were homogenized in 10 volumes of buffered peptone water, and 10-fold dilutions were made in buffered peptone water. For each dilution 6×20 µL drops were inoculated on BGA containing 100 µg/ml streptomycin and after overnight incubation (37° C.) the number of colony-forming units per gram of tissue was determined after counting the bacterial colonies. For samples that were negative after titration, pre-enrichment was performed as described above for the cloacal swabs. Samples that were negative for *Salmonella* presence after titration but positive after *Salmonella* enrichment were presumed to contain $0.5 \times 10^1$ cfu/g. Samples that were negative after enrichment were presumed to have 0 cfu/g. The SPSS 9.0 software was used for statistical analysis. Datasets on *Salmonella* score or *Salmonella* counts were analysed by multivariate ANOVA with days after inoculation and treatment group as independent variables, using the Scheffe error protection for inter-variable comparisons. The nonparametric Kruskal-Wallis test was used to check for inter-treatment effects on *Salmonella* score or *Salmonella* counts at each time point, and in case inter-treatment effects were detected ($P<0.05$), the nonparametric Mann-Whitney test was used to determine significant differences between the control and each of the treatment groups. Datasets on percentages of *Salmonella*-positive swabs were analysed by logistic regression with days after inoculation and treatment group as independent variables. The Cochran-Q test was used to check for inter-treatment effects on percentages of *Salmonella*-positive swabs at each time point, and in case inter-treatment effects were detected ($P<0.05$), the McNemar change test was used to determine significant differences between the control and each of the treatment groups.

To assess the effect of AXOS on intestinal colonisation by *S. enterica* ser. Enteritidis, as a representative of a enteric pathogen, an in vivo infection trial was performed on chickens. Four different treatment groups were compared; the control group was fed a regular wheat-corn-soybean based diet, the second group was fed the control diet base with addition of the short chain AXOS-3-0.25 at 0.2%, and the third and fourth groups received the control diet base supplemented with the medium chain AXOS-9-0.25 at 0.2% and 0.4%, respectively. Inoculation with *Salmonella* was performed when the chicks were 14 days of age, and colonisation of the intestines by *Salmonella* was monitored by taking cloacal swabs from all living animals and by enumerating *Salmonella* in the caeca from a sample of euthanized animals. Cloacal swabs were taken from all animals at the day of inoculation. None of these swabs revealed the presence of *Salmonella*, indicating that there was no infection with *Salmonella* prior to the artificial inoculation.

Figure 1:
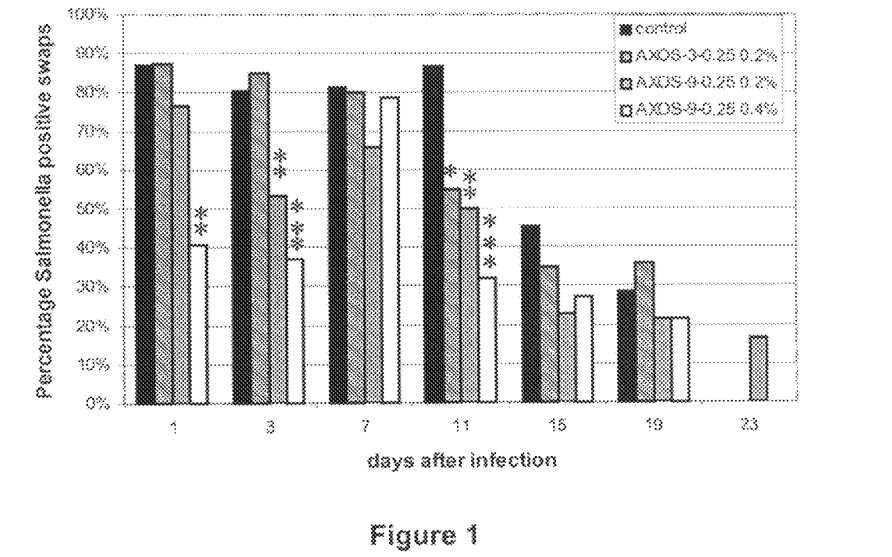
FIG. 1 shows the effects of the addition to chicken feed of 0.2% by weight AXOS-3-0.25, 0.2% by weight AXOS-9-0.25 or 0.4% by weight AXOS-9-0.25 on the percentage of *Salmonella* positive cloacal swabs at different time points after inoculation with *S. enterica* ser. Enteritidis, as measured after direct plating of the swabs. For a given time point the values marked with a symbol above the bars are significantly different from the control group according to the Cochran-Q test (*: P<0.05; : P<0.01; *: P<0.001).
Figure 2:
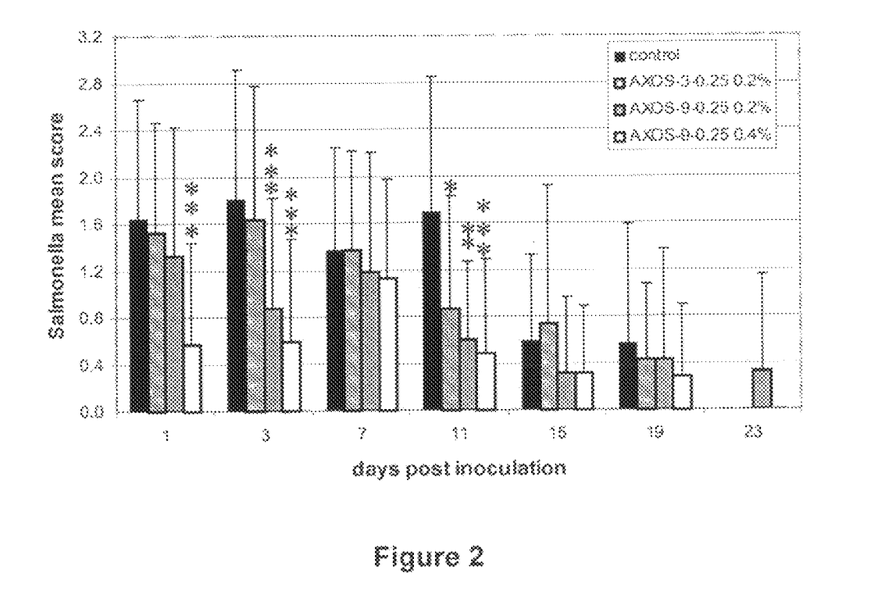
FIG. 2 shows the effects of the addition to chicken feed of 0.2% by weight AXOS-3-0.25, 0.2% by weight AXOS-9-0.25 or 0.4% by weight AXOS-9-0.25 on the *Salmonella* score of cloacal swabs at different time points after inoculation with *S. enterica* ser. Enteritidis. A score of 0 was given for no colonies, 1 for 1 to 10 colonies, 2 for 11 to 100 colonies, 3 for 101 to 1000 colonies, or 4 for more than 1000 colonies of *S. enterica*. Bars represent means of the measurements and error bars indicate the standard deviation. For a given time point the values marked with a symbol above the bars are significantly different from the control group according to the Kruskal-Wallis test (*: P<0.05; : P<0.01; *: P<0.001).

During the period from day 1 to 11 days post infection (dpi), more than 80% of the cloacal swabs in the control group tested positive for *Salmonella* presence, while the percentage of positive swabs steadily declined in the 15-23 dpi period (FIG. 1A). A significant reduction compared to the control group was observed in the 0.4% AXOS-9-0.25 group at 1, 3 and 11 dpi, but not at the 7 dpi time point, and the rate of positive swabs further declined from 15 to 23 dpi as for the control group. A similar decrease in *Salmonella* shedding was observed for the 0.2% AXOS-9-0.25 group, with significant reductions at 3 and 11 dpi compared to the control group. In the AXOS-3-0.25 group, a significant reduction of positive swabs was only noticed at 11 dpi. The presence of *Salmonella* in cloacal swabs was also determined after enrichment of the swabs. With this method, almost 100% of the control group tested positive for *Salmonella* presence in cloacal swabs in the 1-11 dpi period, whereas a significant reduction was seen at 1, 3, and 11 dpi for the 0.4% AXOS-9-0.25 group (data not shown). Data on the *Salmonella* score of the cloacal swabs, reflecting the number of *Salmonella* cfu per swab, are presented in FIG. 2. Highest scores were noted for the control group in the 1-11 dpi period, followed by a decline in the period from 15 to 23 dpi. In the 1-11 dpi period, the *Salmonella* score of the cloacal swabs from the 0.4% AXOS-9-0.25 group reached a peak at 7 dpi at the same level as the control group, yet at all other time points (1, 3 and 11 dpi) the scores were significantly lower than those of the control group. The scores of the 0.2% AXOS-9-0.25 group were intermediate between those of the 0.4% AXOS-9-0.25 and control groups, whereas the 0.2% AXOS-3-0.25 group only showed a significant reduction at 11 dpi.

Figure 3:
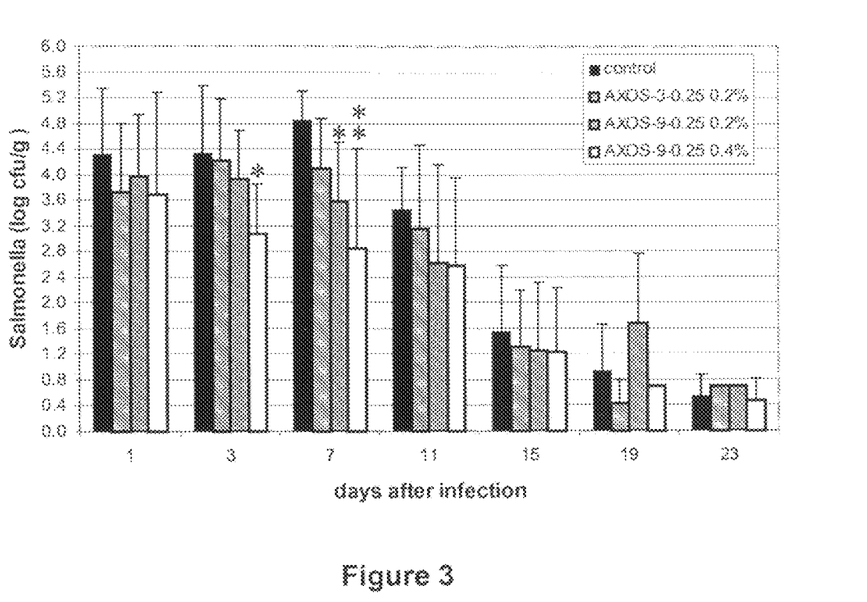
FIG. 3 shows the effects of the addition to chicken feed of 0.2% by weight AXOS-3-0.25, 0.2% by weight AXOS-9-0.25 or 0.4% by weight AXOS-9-0.25 on the occurrence of *Salmonella* in the caecal content at different time points after inoculation with *S. enterica* ser. Enteritidis. Bars represent mean log cfu per g caecal content, and error bars indicate the standard deviation. For a given time point the values marked with a symbol above the bars are significantly different from the control group according to the Kruskal-Wallis test (*: P<0.05; : P<0.01; *: P<0.001).

Measurement of *Salmonella* colonisation of the caecum yielded similar results as provided by the cloacal swab scores (FIG. 3). When analysed over all timepoints by multivariate ANOVA analysis, the reduction in caecal *Salmonella* counts compared to the control group was significant only for the 0.4% AXOS-9-0.25 group ($P<0.001$). The mean log *Salmonella* colony-forming units per g caecal content of the 0.4% AXOS-9-0.25 group was consistently lower relative to the control group throughout the 1-11 dpi period, whereafter the counts dropped to similar low levels for both treatments. At 7 dpi, the apparent peak of infection in the control group, the *Salmonella* counts in the caeca of the 0.4% AXOS-9-0.25 group were 2 log units lower relative to the control group ($P<0.01$). At this time point, a significant reduction of more than 1 log unit was observed in the 0.2% AXOS-9-0.25 ($P<0.05$), whereas the reduction seen in the 0.2% AXOS-3-0.25 group was not significant.

Figure 4:
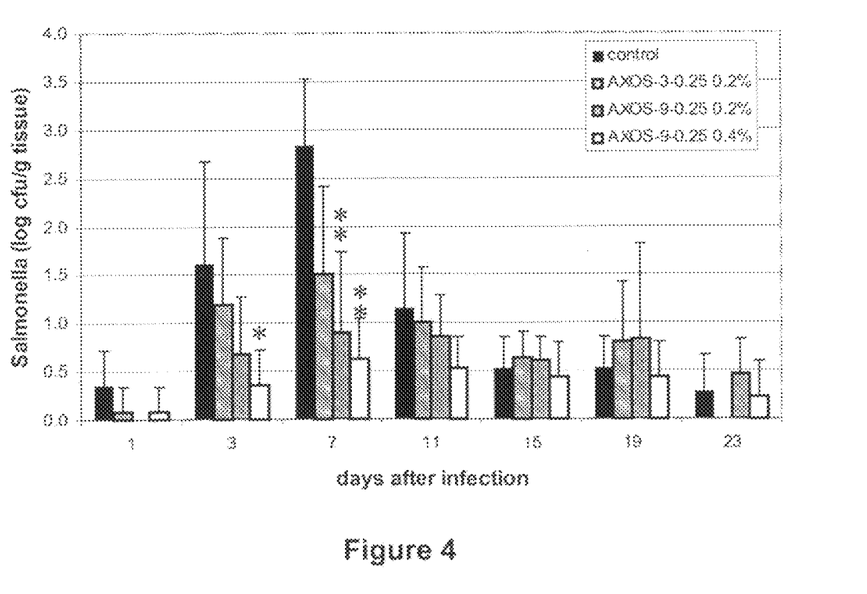
FIG. 4 shows the effects of the addition to chicken feed of 0.2% by weight AXOS-3-0.25, 0.2% by weight AXOS-9-0.25 or 0.4% by weight AXOS-9-0.25 on the occurrence of *Salmonella* in the spleen at different time points after inoculation with *S. enterica* ser. Enteritidis. Bars represent mean log cfu per g spleen tissue, and error bars indicate the standard deviation. For a given time point the values marked with a symbol above the bars are significantly different from the control group according to the Kruskal-Wallis test (*: $P<0.05$; : $P<0.01$; *: $P<0.001$).

The extent of *Salmonella* translocation to internal organs was assessed by measuring the *Salmonella* levels in spleen at different time points after infection (FIG. 4). When analysed over all time points by multivariate ANOVA, a significant reduction in *Salmonella* infection was detected for the 0.4% AXOS-9-0.25 group ($P<0.001$) and the 0.2% AXOS-9-0.25 group ($P=0.003$). At 7 dpi, the peak of colonization, the spleen tissues were less colonized by *Salmonella* in all AXOS treatment groups relative to the control group. The strongest relative decrease in *Salmonella* counts was observed at 7 dpi for the 0.4% AXOS-9-0.25 group, which showed a reduction by more than 2 log units ($P<0.01$), followed by a reduction of about 2 log units for the 0.2% AXOS-9-0.25 group ($P<0.01$), while a trend for reduced infection was seen for the 0.2% AXOS-3-0.25 group ($P=0.1$).

In conclusion, dietary addition of AXOS helps to protect animals from intestinal colonisation of an orally applied bacterial pathogen, as well as systemic translocation of the pathogen to organs. The protection is dose-dependent, since the level of protection was, for all examined tissues, higher in the animals receiving 0.4% dose than those receiving 0.2% of AXOS-9-0.25.

Example 2

Effect of AXOS on Infection of Rats by *Salmonella*

AXOS Preparation.

AXOS-5-0.20 was prepared from wheat bran by extraction with a glycosyl hydrolase family (GHF) 10 endoxylanase as previously described (Swennen et al. cited supra), except that the step of protease treatment of the bran was omitted. This preparation had an average degree of polymerisation of 5 and an arabinose to xylose ratio of 0.20.

Study Design.

6-week-old male rats (Wistar) are purchased from Elevage Janvier (Le Genest-St-Isle, France) and randomly assigned to 3 groups of 8 rats each. The rats are housed in stainless steel wire-bottom cages in an environmentally controlled room (22° C.) with a 14-10 hours light-dark cycle. Rats are given free access to water and to pellets (10 mm) of the 'control' diet (Table 4) during 6 days. After 6 days of adaptation on the control diet, the rats are randomly assigned to one of 3 different treatment groups, and the groups are each given free access during 10 days to pellets (10 mm) of one of the 3 diets described in Table 4, respectively, a control diet, a 2.5% AXOS diet and a 5% AXOS diet.

Animals were weighed and feed intake is measured 3 times per week. After said 10 days, all animals are orally infected with a clinical isolate of Salmonella enteridis, as described by Bovee-Oudenhoven et al. in Gastroenterology (1997) 113: 550-7. The animals are infected in the morning by gastric gavage with 0.5 ml of saline containing 3% (wt/vol) sodium bicarbonate with $5 \times 10^8$ viable S. Enteridis. The day before infection and 1, 3, 6 and 9 days after Salmonella infection, fresh faecal samples are collected. The number of Salmonella in the faeces are quantified by plating on Modified Brilliant Green Agar as previously described (Giaffer et al., 1991). Throughout the infection experiment the rats of each experimental group are fed their respective experimental diet.

In a second infection experiment with rats the effect of administration of AXOS in the feed on translocation to the spleen at day 2 after infection is investigated. The experimental set-up is similar to that described above. At the section day the animals are sacrificed and the spleen is aseptically removed, weighed and homogenized in sterile saline (10-fold dilution) and plated on Brilliant Green Agar for counting as described in (Oudenhove et al., 1994). Viable Salmonella counts are expressed as the total log 10 colony-forming units in the spleen.

The study shows a reduction of the fecal Salmonella excretion in the groups fed an arabinoxylo-oligosaccharide-containing diet, illustrating a stimulating effect of the arabinoxylo-oligosaccharides on the colonization resistance against Salmonella. The study further provides an indication that the oral administration of arabinoxylo-oligosaccharides to rats reduces the translocation of Salmonella to internal organs and more particularly to the spleen.

Example 3

Effect of Daily Intake of Different Dosages of AXOS on Gastro-Intestinal Complaints in Healthy Human Volunteers AXOS Preparation.

AXOS-5-0.20 was prepared from wheat bran by extraction with a glycosyl hydrolase family (GHF) 10 endoxylanase as previously described (Swennen et al. 2006), except that the step of protease treatment of the bran was omitted. This preparation had an average degree of polymerisation of 5 and an arabinose to xylose ratio of 0.20.

Subjects

Sixty healthy volunteers (men and women; age ranging between 18 and 80 years) are included in the study. None of the subjects had severe gastrointestinal complaints in the 3 months prior to the start of the study and had ever had abdominal surgery. They have been free of antibiotics or any other medical treatment influencing gut transit or the intestinal flora for at least 3 months before the start of the study. During the study the volunteers are urged to have a regular eating pattern (3 meals per day) and the intake of fermented milk products containing living bacteria or the intake of compounds known to modulate the composition of the intestinal flora is forbidden.

Study Design.

Figure 5:
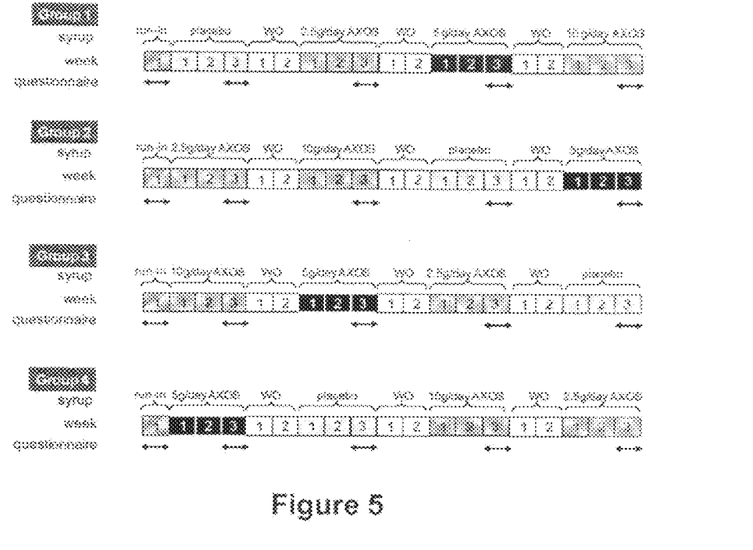
FIG. 5 schematically shows an overview of the study design of a clinical trial evaluating the effect of the daily intake of different dosages of arabinoxylo-oligosaccharides (AXOS) on gastro-intestinal complaints in healthy human volunteers (WO=wash out).

The duration of the entire clinical trial is 19 weeks. The clinical trial starts with a run-in period of 1 week, followed by 4 administration periods of 3 weeks each, with a wash out period of 2 weeks between the administration periods. In the course of the study all volunteers receive three dosages of AXOS-5-0.20 (2.5 g/day, 5.0 g/day and 10 g/day) and a placebo. The volunteers are divided into four groups in a random manner, with the same number of persons in each group, following a double blind protocol. The various treatments are assigned to the groups according to a 4×4 'Latin Square design', allowing the order of the treatments to be different for every group. The study design is schematically presented in FIG. 5.

During the administration periods, the volunteers are asked to consume 20 ml of a specific type of syrup at breakfast and in some administration periods an additional 20 ml at diner, this according to the intake scheme specified in Table 2. The compositions of the syrups used in the study is given in Table 3.

During the one-week run-in period and the last week of each intake period (AXOS or placebo), the volunteers are asked to fill in a questionnaire on a daily basis. The questions herein are designed to evaluate the occurrence and gravity of symptoms reflecting gastrointestinal complaints. The questions interrogate the volunteers on the occurrence of mild gastrointestinal discomfort, such as bloating or increased flatulence, as well as on more serious complaints, such as abdominal cramps, diarrhea and vomiting.

The outcome of the study indicates that the oral administration of arabinoxylo-oligosaccharides improves to overall gastrointestinal well being and lowers the occurrence of gastrointestinal discomfort and attenuates the gravity thereof. This suggests a better protection against gastrointestinal infection as a result of the intake of the arabinoxylo-oligosaccharides.

TABLE 1

| Feedstuffs | % |
| --- | --- |
| Wheat | 48.23 |
| Yellow corn | 10.00 |
| Soybean meal-48 | 23.63 |
| Heat full-fat soybean | 8.50 |
| Rendered animal fat | 4.59 |
| Soybean oil | 1.25 |
| Calcium carbonate | 0.56 |
| Calcium monohydrogen phosphate | 1.27 |
| Sodium chloride | 0.29 |
| Phytase (Ronozyme) | 0.02 |
| Sodium hydrogencarbonate | 0.09 |
| L-Lysine•HCl | 0.28 |
| DL-Methionine | 0.23 |
| L-Threonine | 0.09 |
| Vitamin & trace el. premix | 1.00 |
| sum | 100.00 |
| Composition | |
| Metabolisable energy for broilers, MJ/kg | 12.40 |
| Crude protein, % | 20.75 |

TABLE 1-continued

|  | % |
|---|---|
| Digestible lysine, % | 1.13 |
| Digestible sulphuric amino acids, % | 0.79 |
| Digestible threonine, % | 0.73 |
| Calcium, % | 0.94 |
| Available phosphorous, % | 0.44 |
| Cation-anion balance (Na+K—Cl), meq/kg | 223.00 |
| Linoleic acid, % | 2.53 |

TABLE 2

Administration scheme for the AXOS and placebo syrups

| | Treatment | | | |
|---|---|---|---|---|
| | Placebo | 2.5 g/dag AXOS | 5 g/dag AXOS | 10 g/dag AXOS |
| Breakfast | 20 ml placebo syrup | 20 ml AXOS syrup 2 (=2.5 g AXOS preparation) | 20 ml AXOS syrup 1 (=5 g AXOS preparation) | 20 ml AXOS syrup 1 (=5 g AXOS preparation) |
| Dinner | / | / | / | 20 ml AXOS syrup 1 (=5 g AXOS preparation) |

TABLE 3

Composition of syrups containing AXOS and placebo

|  | Placebo syrup | AXOS syrup 1 | AXOS syrup 2 |
|---|---|---|---|
| AXOS-preparation (g/l) | 0 | 250 | 125 |
| Sucrose (g/l) | 875 | 625 | 750 |
| Carrageenan (g/l) | 10 | 0 | 0 |
| Colouring agent (ml/l) | 3 | 3 | 3 |
| Flavor (ml/l) | 6 | 6 | 6 |
| Citric acid (mg/l) | 288 | 480 | 384 |
| K-sorbate (mg/l) | 200 | 200 | 200 |
| Water (g) | 365 | 365 | 365 |
| TOTAL | 1000 ml | 1000 ml | 1000 ml |
| TOTAL | 1250 g | 1250 g | 1250 g |

TABLE 4

Composition of the different rat diets (in g per 100 g).

|  | control | AXOS 2.5% | AXOS 5% |
|---|---|---|---|
| Corn starch (pre-gelatinised) | 73.50 | 71.00 | 68.50 |
| AXOS preparation | — | 2.50 | 5.00 |
| Soy protein isolate | 10.80 | 10.80 | 10.80 |
| Wheat gluten | 5.00 | 5.00 | 5.00 |
| Soybean oil | 3.50 | 3.50 | 3.50 |
| L-Lysine | 0.45 | 0.45 | 0.45 |
| DL-Methionine | 0.15 | 0.15 | 0.15 |
| L-Cystine | 0.08 | 0.08 | 0.08 |
| L-Threonine | 0.13 | 0.13 | 0.13 |
| L-Tryptophan | 0.07 | 0.07 | 0.07 |
| Vitamin premix | 1.00 | 1.00 | 1.00 |
| Mineral/trace elem. premix | 4.20 | 4.20 | 4.20 |
| Calcium carbonate | 0.70 | 0.70 | 0.70 |
| $Cr_2O_3$ | 0.20 | 0.20 | 0.20 |
| Choline chloride | 0.20 | 0.20 | 0.20 |
| Butylhydroxytoluol | 0.02 | 0.02 | 0.02 |

The invention claimed is:

1. A method for reducing the infection of a non-human animal or a human being with *Salmonella* and reducing the translocation of said *Salmonella* towards internal organs, wherein said method comprises enterally administering a composition comprising an effective amount of an active ingredient, wherein said active ingredient consists of arabinoxylo-oligosaccharides having an average degree of polymerization between 3 and 50 and an average degree of substitution between 0.15 and 0.35.

2. The method according to claim 1, wherein said arabinoxylo-oligosaccharides are administered to said non-human animal through an animal feed.

3. The method according to claim 2, wherein the animal feed is supplemented with between 1 and 50 g of arabinoxylo-oligosaccharides per kg of feed.

4. The method according to claim 3, wherein the animal feed is supplemented with between 1 and 10 g of arabinoxylo-oligosaccharides per kg of feed.

5. The method according to claim 2, wherein said non-human animal is poultry or a lifestock animal.

6. The method according to claim 2, wherein said non-human animal is a pet animal.

7. The method according to claim 6, wherein said arabinoxylo-oligosaccharides are administered to the pet animal by feeding the animal a pet food comprising between 0.25 and 5 g of arabinoxylo-oligosaccharides per daily serving of said pet food.

8. The method according to claim 6, wherein said arabinoxylo-oligosaccharides are administered to the pet animal by feeding the animal a pet treat food comprising between 0.25 and 5 g of arabinoxylo-oligosaccharides per serving of said pet treat food.

9. The method according to claim 6, wherein said pet is a dog or a cat.

10. The method according to claim 1, wherein said arabinoxylo-oligosaccharides are ad ministered to said human being at a daily dose between 0.25 g and 10 g of arabinoxylo-oligosaccharides.

11. The method according to claim 10, wherein said arabinoxylo-oligosaccharides are administered at a daily dose between 0.5 g and 5 g of arabinoxylo-oligosaccharides.

12. The method according to claim 10, wherein said arabinoxylo-oligosaccharides are administered in a food product or non-alcoholic beverage.

13. The method according to claim 12, wherein said food product or non-alcoholic beverage is a cereal-based product comprising at least 25% of cereals or cereal-derived material.

14. The method according to claim 10, wherein said arabinoxylo-oligosaccharides are administered in a food supplement.

* * * * *

UNITED STATES PATENT AND TRADEMARK OFFICE
CERTIFICATE OF CORRECTION

PATENT NO.        : 9,061,046 B2
APPLICATION NO.   : 12/680435
DATED             : June 23, 2015
INVENTOR(S)       : Willem Broekaert et al.

It is certified that error appears in the above-identified patent and that said Letters Patent is hereby corrected as shown below:

In the Specification

Column 1, line 62, replace "☐-L-arabino-furanosyl" with --α-L-arabino-furanosyl--.

In the Claims

Column 14, Claim 5, Line 29, replace "lifestock" with --livestock--;

Claim 10, Line 45, replace "ad ministered" with --administered--.

Signed and Sealed this
Seventeenth Day of November, 2015

Michelle K. Lee
*Director of the United States Patent and Trademark Office*